US008148677B2

(12) United States Patent
Zhang et al.

(10) Patent No.: US 8,148,677 B2
(45) Date of Patent: Apr. 3, 2012

(54) PEPTIDE IDENTIFICATION AND QUANTITATION BY MERGING MS/MS SPECTRA

(75) Inventors: Qiang Zhang, Saratoga, CA (US); Roza I. Viner, Fremont, CA (US); Torsten Ueckert, Bremen (DE); Vladimir Zabrouskov, Santa Clara, CA (US)

(73) Assignee: Thermo Finnigan LLC, San Jose, CA (US)

( * ) Notice: Subject to any disclaimer, the term of this patent is extended or adjusted under 35 U.S.C. 154(b) by 563 days.

(21) Appl. No.: 12/187,219

(22) Filed: Aug. 6, 2008

(65) Prior Publication Data
US 2009/0194682 A1  Aug. 6, 2009

Related U.S. Application Data

(60) Provisional application No. 61/026,434, filed on Feb. 5, 2008.

(51) Int. Cl.
H01J 49/26 (2006.01)
G06F 17/00 (2006.01)
G06F 17/30 (2006.01)

(52) U.S. Cl. ............. 250/282; 250/281; 702/27; 702/22
(58) Field of Classification Search .................. 250/281, 250/288, 290–293; 702/19, 22, 27
See application file for complete search history.

(56) References Cited

U.S. PATENT DOCUMENTS

| | | | |
|---|---|---|---|
| 6,963,807 B2 * | 11/2005 | Townsend et al. | 702/27 |
| 7,880,136 B2 * | 2/2011 | Makarov et al. | 250/282 |
| 2002/0102610 A1 * | 8/2002 | Townsend et al. | 435/7.1 |
| 2002/0173920 A1 * | 11/2002 | Xu et al. | 702/27 |
| 2004/0102688 A1 * | 5/2004 | Walker et al. | 600/407 |
| 2004/0108452 A1 * | 6/2004 | Graber et al. | 250/281 |
| 2008/0048109 A1 * | 2/2008 | Schwartz et al. | 250/282 |
| 2008/0203288 A1 * | 8/2008 | Makarov et al. | 250/282 |
| 2009/0238808 A1 * | 9/2009 | Drewes et al. | 424/94.1 |

OTHER PUBLICATIONS

Monigatti et al., "SALAMI—Spectrum Alignments using Accurate Mass and High-Sensitivity Data," Proceedings of the 55th ASMS Conference on Mass Spectrometry and Allied Topics, Jun. 3-7, 2007 in Indianapolis, Indiana.
Yates et al., "Performance of a Linear Ion Trap-Orbitrap Hybrid for Peptide Analysis," Analytical Chemistry, vol. 78, No. 2, XP002526482, pp. 493-500, (2006).
Mayrhofer et al., "Comparison of Vacuum Matrix-Assisted Laser Desorption/Ionization (MALDI) and Atmospheric Pressure MALDI (AP-MALDI) Tandem Mass Spectrometry of 2-Dimensional Separated and Trypsin-Digested Glomerular Proteins for Database Search Derived Identification," Journal of Proteome Research, 2006, 5, pp. 1967-1978.

* cited by examiner

Primary Examiner — Bernard E Souw
(74) Attorney, Agent, or Firm — Michael C. Staggs

(57) ABSTRACT

The present invention is directed to methods of merging spectral data resulting from collision fragmentation processes, such as, for example, Pulsed Q Dissociation (PQD), high-energy collision-induced dissociation (HCD), electron transfer disassociation (ETD), collision-induced dissociation (CID), and photo-dissociation processes, such as, but not limited to, infrared multi-photon photo-dissociation (IRMPD), to provide the desired qualitative and quantitative information on a single peptide. By merging such ETD, CID, or IRMPD scans with corresponding HCD scans that are obtained on the same precursor, the quality of the resulting spectrum is increased so as to provide more confident identification of peptides and correspondingly the quantification is enhanced because the HCD method of the MS/MS spectrum produces higher abundances of detectable reporter ions. Such methods, as disclosed herein, are especially applicable for peptides which experience predominant neutral loss in the ion trap, e.g., phosphorylated.

22 Claims, 3 Drawing Sheets

PEPTIDE IDENTIFICATION AND QUANTITATION BY MERGING MS/MS SPECTRA

CROSS-REFERENCE TO RELATED APPLICATIONS

This application claims priority under 35 USC §119(e) to U.S. Provisional Patent Application 61/026,434 filed 5 Feb. 2008, entitled "Improved Peptide Identification and Quantitation by Merging MS/MS Spectra", the entirety of which is incorporated by reference herein.

FIELD OF THE INVENTION

The present invention relates to the biotechnology field, and more particularly to the field of peptide proteomics involving improved methods for peptide identification and quantification using tandem MS/MS spectroscopy.

DISCUSSION OF THE RELATED ART

Proteomics is the study of patterns of protein expression by complex biological systems. Generally, it involves the determination of the relative abundance, post-translational modification, and/or stability of large numbers of cellular proteins at specific time-points within the life cycle of an organism.

Mass spectrometry (MS) is the study of gas phase ions as a means to characterize the structures and identities of molecules. Proteomics began with the commercialization of soft ionization techniques, such as, for example, electrospray ionization (ESI) and matrix assisted laser desorption ionization (MALDI), which permitted analysis of such proteins. As part of the evolution of mass spectroscopy, commercial high performance MS instruments were developed for structural characterization of such soft ionization techniques and have proven to be successful at identifying proteins even down to about the sub picomolar levels.

One such commercial high performance instrument(s) involves tandem mass spectrometry (MS/MS). Such an instrument/technique provides a means for fragmenting a mass-selected ion and measuring the mass to charge ratio (m/z) of the daughter product ions that are produced during the fragmentation process. Such a method often uses collision-induced dissociation (CID), wherein a mass-selected ion is transmitted to a high-pressure region so as to be subjected to low energy collisions with introduced inert gas molecules. Thereafter, as a molecular ion collides, a portion of its kinetic energy is converted into excess internal energy so as to render the ion unstable, which results in unimolecular fragmentation reactions prior to leaving a configured collision cell Qualifying as well as quantitating fragmentation reactions are important aspects of proteomics research. With respect to qualification of the fragmented peptides, resultant observed mass spectra are typically searched to qualify the peptides and hence identify the proteins in the original mixture, either by automated correlation of uninterpreted CID spectra with a sequence database or by searching sequence data bases with complete or partial peptide sequences obtained by manual or computer assisted interpretation of the CID data. For example, the SEQUEST program (Eng et al.) uses uninterpreted product ion spectra to search databases of theoretical spectra derived from protein and translated gene sequence databases. SEQUEST first generates a list of theoretical peptide masses for each entry in the database that match the experimentally determined peptide mass, producing a list of candidate peptides. The program then calculates the fragment ion masses expected for each of the candidate peptides and generates predicted MS/MS spectra. The experimentally determined MS/MS spectrum is then compared with the predicted spectra using a correlation function. Each comparison receives a score, and the highest-scoring peptide(s) are reported. When high scoring matches are detected, one effectively jumps from spectral data to peptide identity. A protein is then positively identified when the one or more peptides can be matched unambiguously.

With respect to quantitation, both labeling and non-labeling approaches have been explored, wherein among the labeling techniques, the amine-reactive isobaric (iTRAQ™) technique is particularly widely used. In such a beneficial technique, peptides are labeled with isobaric tags that produce low mass reporter ions during, for example, MS/MS fragmentation processes as briefly described above. The abundance of the reporter ions is then utilized as the primary criterion for reliable and reproducible fragmentation data in order to provide the quantification information desired from the measurements. However, while such MS/MS peptide fragmentation techniques are highly efficient, the resultant MS/MS spectra often have relatively low mass accuracy and resolution. Furthermore, low-mass fragment ions are not trapped, making certain small fragmented ions un-observable, which often leads to uninformative spectra.

To improve the quantitation and qualification of resultant MS/MS spectra of desired fragmented peptides, hybrid mass spectrometers such as the LTQ Orbitrap (available from Thermo Fisher Scientific (Bremen) GmbH), have been developed to provide for dissociation techniques that results in complimentary MS/MS fragmentation data. Such techniques include a high-energy collision-induced dissociation (HCD) method, in which the precursor ions are accelerated to high velocities into a gas-filled collision cell, and a low-energy collision-induced dissociation (in-trap CID) method as similarly discussed above, in which the precursor ions are resonantly excited within the ion trap and undergo collisions with atoms or molecules of a damping gas.

However, while the HCD method generally produces higher abundances of detectable reporter ions in the MS/MS spectrum, which enhances quantitation, such a method can compromise the intensity of sequence ions and thereby decrease the confidence of peptide identifications. Conversely, the in-trap CID method, which produces a greater abundance of sequence ions in an MS/MS spectrum, yields lower abundances of detectable low-mass reporter ions, which decrease the accuracy and reproducibility of quantitation.

Accordingly, a need exists for an approach that takes advantage of similar complimentary methods so as to simultaneously improve peptide identification as well as quantification when using the various instruments as disclosed herein. The present invention is directed to such a need.

SUMMARY OF THE INVENTION

Accordingly, the present invention provides a method for identification and quantification of one or more proteins in a mixture, including: generating a raw file; identifying a corresponding in-trap induced MS/MS spectra and a high-energy collision-induced dissociation (HCD) spectra resulting from the raw file; merging the identified data from the raw file into a spectrum; utilizing the merged spectrum to initiate a database search; and exporting results that match the database search so as to simultaneously quantify and qualify the one or more proteins from said mixture.

In another aspect of the present invention, the present invention provides a method for identification and quantification of one or more proteins in a mixture, including: generating a raw file; identifying a corresponding in-trap induced MS/MS spectra and a high-energy collision-induced dissociation (HCD) spectra resulting from the raw file; utilizing the identified in-trap induced spectra to initiate a database search; merging a matched in-trap spectra resulting from the database search with the high energy collision induced (HCD) spectra from the raw file into a spectrum; and exporting results of the merged spectrum so as to simultaneously quantify and qualify the one or more proteins from the mixture.

Another aspect of the present invention includes a computer readable medium that provides instructions. When the instructions are executed on a processor, such instructions can cause the processor to perform a method of controlling a mass spectrometer for identification and quantification of one or more proteins in a mixture that includes: generating a raw file; identifying a corresponding in-trap induced MS/MS spectra and a high-energy collision-induced dissociation (HCD) spectra resulting from the raw file; merging the identified data from the raw file into a spectrum; utilizing the merged spectrum to initiate a database search; and exporting results that match the database search so as to simultaneously quantify and qualify the one or more proteins from said mixture.

A final aspect of the present invention includes a computer readable medium that provides instructions. When the instructions are executed on a processor, such instructions can cause the processor to perform a method of controlling a mass spectrometer for identification and quantification of one or more proteins in a mixture that includes: generating a raw file; identifying a corresponding in-trap induced MS/MS spectra and a high-energy collision-induced dissociation (HCD) spectra resulting from the raw file; utilizing the identified in-trap induced spectra to initiate a database search; merging a matched in-trap spectra resulting from the database search with the high energy collision induced (HCD) spectra from the raw file into a spectrum; and exporting results of the merged spectrum so as to simultaneously quantify and qualify the one or more proteins from the mixture.

Accordingly, the present invention provides for an improved method of peptide identification and quantitation of complex protein mixtures in tandem mass spectrometer systems. In particular, because of the techniques disclosed herein, the quality of the resulting spectrum is increased so as to provide more confident identification of peptides and correspondingly the quantification is enhanced because the HCD method of the MS/MS spectrum produces higher abundances of detectable reporter ions. Such methods, as disclosed herein, are beneficial in applications, such as, but not limited to, in-vitro sample analysis, proteomics analysis, complex sample analysis, and are especially beneficial in applications for desired detection of peptides which experience predominant neutral loss in an ion trap.

DETAILED DESCRIPTION

Figure 1:
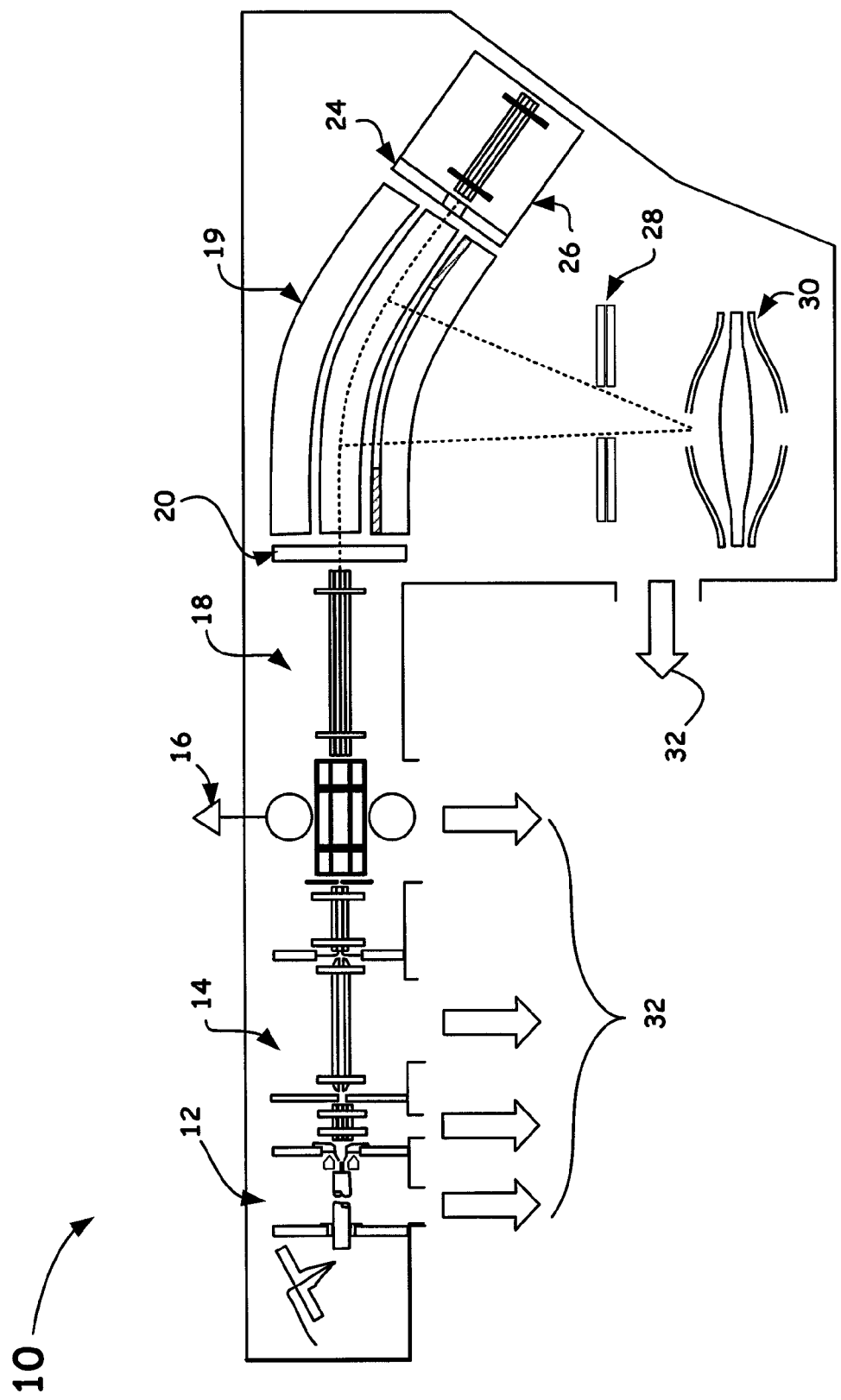
FIG. 1 is an exemplary configuration of a spectrometer instrument capable of being utilized in the present invention.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Moreover, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

General Description

The present invention is directed to a novel method of merging high quality and accurate MS/MS spectra of any MS-order, i.e., $MS^n$, more often $MS^2$, with high abundance and resolution data of reporter ions, such as, but not limited to, iTRAQ and/or Tandem Mass Tag (TMT) reporter ions, so as to provide simultaneous peptide identification and quantitation in complex protein digests.

In particular, the present provides such qualitative and quantitative information by utilizing a high-energy collision-induced dissociation (HCD) process that capitalizes on the use of such reporter ions in combination with in-trap methods, such as, but not limited to, electron transfer dissociation (ETD), collision-induced dissociation (CID), Pulsed Q Dissociation (PQD), and photo-dissociation processes, such as, but not limited to, infrared multi-photon photo-dissociation (IRMPD). By merging captured spectra resulting from such in-trap fragmentation processes with corresponding HCD fragmentation scans that are obtained on the same precursor, the quality of the resulting spectrum is increased so as to provide more confident identification of peptides and correspondingly the quantification is enhanced because the HCD method of the MS/MS spectrum produces higher abundances of detectable reporter ions.

To produce such data, a hybrid mass spectrometer (e.g., LTQ Orbitrap or an LTQ Orbitrap XL™ from Thermo Fisher Scientific) can be utilized and configured to operate in a reduced cycle time mode so as to enable accurate measurement of a precursor mass, i.e., as measured in an Orbitrap, concurrent with high sensitivity Data Dependent MS/MS scans in an ion trap which is configured with a precursor window that enables simultaneous fragmentation of desired light and heavy peptides. Thereafter, one or more Data Dependent HCD MS/MS scans can be implemented on the same precursors as for the ion trap MS/MS scans with the length of the HCD scan being only slight longer that that of the ion trap MS/MS scan. The resulting multiplex MS/MS data is then capable of being merged using the novel techniques embodied in custom or available commercial software (e.g., Mascot) to provide for the desired simultaneous protein identification and quantification.

Specific Description

FIG. 1 shows a beneficial configuration of a spectrometer instrument, shown generally designated by the reference numeral 10, which is capable of being utilized with the methods of the present invention. Often, the spectrometer 10, as generally shown in FIG. 1, is configured as a hybrid linear ion trap/Orbitrap mass spectrometer (e.g., a commercially available LTQ Orbitrap or an LTQ Orbitrap XL™ mass spectrometer provided by Thermo Fisher Scientific (Bremen) GmbH) so as to best implement the merged protein quantitiation/qualification beneficial data techniques of the present invention.

Generally described, mass spectrometer 10, can include an ion source 12, such as, but not limited to, an Electrospray Ionization Source (ESI), a Nanoelectrospray Ionization source (NanoESI), or an Atmospheric Pressure Chemical Ionization source (APCI)) for producing ions, such as ions resulting from a sample stream (e.g., from the eluate of a liquid chromatograph). Such ions are then directed to coupled instruments as known to those of ordinary skill in the art, such as, a multipole device often configured as a two-dimensional quadrupole ion trap mass analyzer 16, and correspondingly to a mass analyzer 30, such as an Orbitrap mass analyzer.

In being directed to the example mass analyzers 16 and 30, the resultant ions are transported through a series of chambers of progressively reduced pressure by a set of ion optic components 14 (e.g., electrostatic lenses, and multipoles selected from radio-frequency RF quadrupole and octopole ion guides) that guide and focus ions to provide good transmission efficiencies. The various chambers communicate with corresponding ports 32 (represented as arrows in the figure) that are coupled to a set of pumps (not shown) to maintain the pressures at the desired values. The operation of mass spectrometer 10 is controlled and data is acquired and processed by a control and data system (not depicted), which may be implemented as any one or a combination of general or special-purpose processors, firmware, software (e.g., Discoverer Software), and hardware circuitry configured to execute a set of instructions that embody the prescribed data analysis and control routines of the present invention. Such processing of the data may also include averaging, scan grouping, deconvolution, library searches, data storage, and data reporting.

It is also to be appreciated that instructions to start predetermined scans, the identifying of a set of m/z values within the raw file from a corresponding scan, the merging of data, the exporting/displaying of results, etc., may be executed under instructions stored on a machine-readable medium (e.g., a computer readable medium) coupled to the mass spectrometer 10. A computer-readable medium, in accordance with aspects of the present invention, refers to mediums known and understood by those of ordinary skill in the art, which have encoded information provided in a form that can be read (i.e., scanned/sensed) by a machine/computer and interpreted by the machine's/computer's hardware and/or software. When, for example, mass spectra data of a mass spectrum is received by the apparatus disclosed herein, the information embedded in a computer program of the present invention can be utilized, for example, to extract data (e.g., HCD and CID data) from the mass spectral data, which corresponds to a selected set of mass-to-charge ratios. In addition, the information embedded in a computer program of the present invention can be utilized to carry out methods for normalizing, shifting data, or extracting unwanted data from a raw file in a manner as disclosed herein.

To illustrate an example arrangement of the present invention, the selected peptide or protein precursor ions are often isolated in ion trap mass analyzer 16 and fragmented within using any known photo-dissociation processes such as, but not limited to, infrared multi-photon photo-dissociation (IRMPD), but more often, such peptide or protein precursor ions are fragmented using known dissociation methods, such as, but not limited to, Pulsed Q Dissociation (PQD), electron transfer dissociation (ETD), and/or collision-induced dissociation (CID). When using in-trap CID as the qualitative fragmentation process, resonantly excited ions collide with atoms or molecules of damping gas residing within the trap interior and undergo dissociation. The ion trap 16 is then often operated in the analytical scan mode to acquire an MS/MS spectrum of the product ions. When operated with HCD, the precursor ions arranged to be isolated in ion trap mass analyzer 16 are then ejected from the ion trap (via the exit end thereof) by reducing the voltage at the back aperture of the ion trap 16 so as to accelerate into a transport multipole 18, such as for example a quadrupole, a hexapole, but most often an octopole instrument for guiding such precursors. Thereafter, a second multipole device 19, often configured as a C-trap, and often maintained at a nitrogen pressure of about 1 mTorr receives the ejected ions and passes such ions at accelerated high velocities (e.g., by application of the appropriate DC offset voltages, or by generation of an axial DC field within the multipole interior). As part of the HCD process, the accelerated ions then undergo highly energetic collisions with atoms or molecules of collision gas (up to about 5 mbar nitrogen) within a collision cell 26, e.g., a multipole device often configured as an octopole. The predetermined ions then fragment into product ions and are then returned to multipole 19 to be accumulated and confined by voltages on the gate aperture 20 and trapping plate 24. Thereafter, multipole device 19 ejects such trapped ions radially, via for example, turning off an applied RF, and such ions are further directed by configured ion optics 28 (i.e., lenses) toward a configured mass analyzer, often an Orbitrap mass analyzer 30. Orbitrap mass analyzer 30 may then be operated to acquire an MS/MS spectrum of the product ions.

Figure 2:
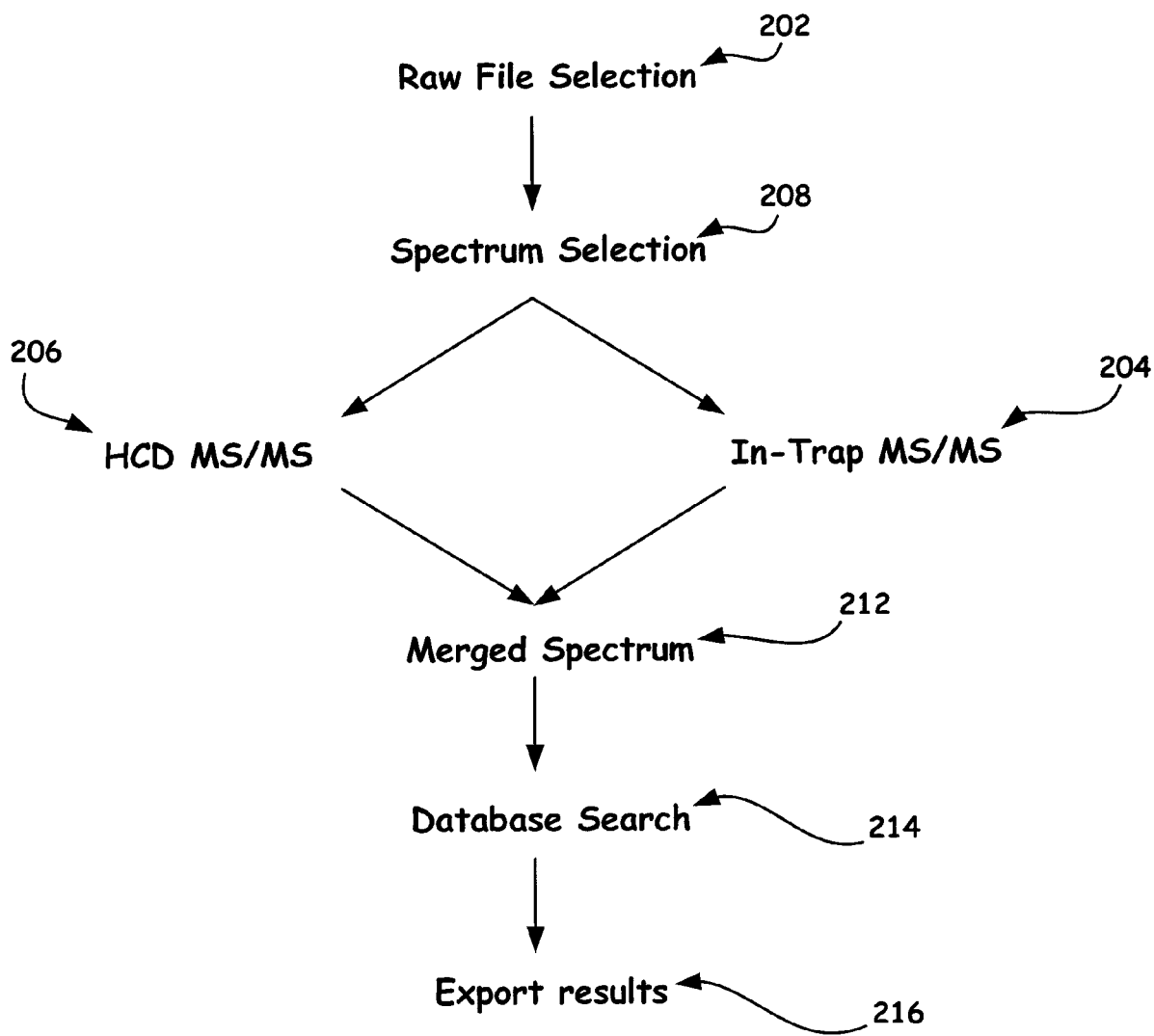
FIG. 2 shows a flow chart representation of a first data merging approach of the present invention.

FIG. 2 is a flowchart depicting an example approach for quantitation and structural identification of proteins by MS/MS analysis, in accordance with an illustrative embodiment of the present invention. Initially, a set of raw files 202 are often generated representative of the MS/MS spectra of selected peptide precursor ions. For each of the selected ions, MS/MS spectra are acquired using both in-trap fragmentation processes 204, e.g., ETD, CID, PQD, etc., (with the spectra acquired by the ion trap) and an HCD fragmentation process 206 (with the spectra acquired by the Orbitrap). Selection 208 of precursor ions may be performed in a data-dependent manner, i.e., by automatic selection of ions from a full scan MS spectrum using criteria of, for example, intensity, charge state, minimum/maximum mass-to-charge ratio (m/z), or user-specified inclusion/exclusion lists. Following acquisition of the MS/MS spectra and generation of the raw file, the control and data system processes the raw file to identify corresponding MS/MS spectra (MS/MS spectra obtained for the same precursor ion) acquired using the in-trap fragmentation and HCD methods. After the corresponding MS/MS spectra have been identified, the spectra are combined into a merged spectrum 212 by adding the associated data contained in the raw files after normalization of the data in predetermined situations where the absolute intensities of in-trap and HCD spectra are vastly different.

In particular, and as known by those of ordinary skill in the art, the raw files contain, for each analytical scan number, a set of (m/z, intensity) points representative of the abundance of ions at a particular value of m/z. Combining of spectra to create the merged MS/MS spectrum is often performed by adding the intensity values appearing in the HCD and in-trap spectra for given values of m/z. However, in an example operation of the present invention, after the corresponding MS/MS spectra have been identified and prior to adding such intensity values, the spectra are first normalized and then combined into a desired merged spectrum by adding the normalized associated data contained in the raw files. With respect to the normalization procedure, the method of operation simply takes the intensity of the largest peak in a given spectrum (i.e., "the base peak") and arbitrarily sets this intensity as 100. Every peak in the given spectrum is then normalized to that intensity of the base peak. Thus the intensity of every peak in the given spectrum is replaced by the normalized intensity according to:

normalized_intensity=100*intensity/base_peak_intensity

As stated above however, such a normalization of spectra can but does not have to be applied to all in-trap spectra and HCD spectra prior to merging them together. A reason for including a means to normalize spectra before merging identified data from a raw file is that the absolute intensities of in-trap and HCD spectra can be quite different.

In addition to normalizing the raw data, it may also be beneficial to filter the data in the respective MS/MS spectra (e.g., to remove data falling below a specified signal-to-noise ratio) prior to adding the data. Moreover, it may be beneficial to correct for phenomena such as chemical mass shift (which may occur to a significantly greater degree in the ion trap mass analyzer) to ensure alignment of m/z values in the spectra prior to adding the data. The merged MS/MS spectrum, which includes both high-intensity low-mass reporter ions (from the HCD spectrum) and high-intensity sequence ions (from, for example, the in-trap CID or ETD spectrum) is used for a database search 214. Often, a database tool such as, SEQUEST or MASCOT, which can perform both quantitation and protein identification functions, is utilized for the database search. It has been observed that exported results 216 obtained using a merged spectrum offer both reliable quantitation and high numbers of identified proteins, thus providing better quantitative statistics per protein.

Figure 3:
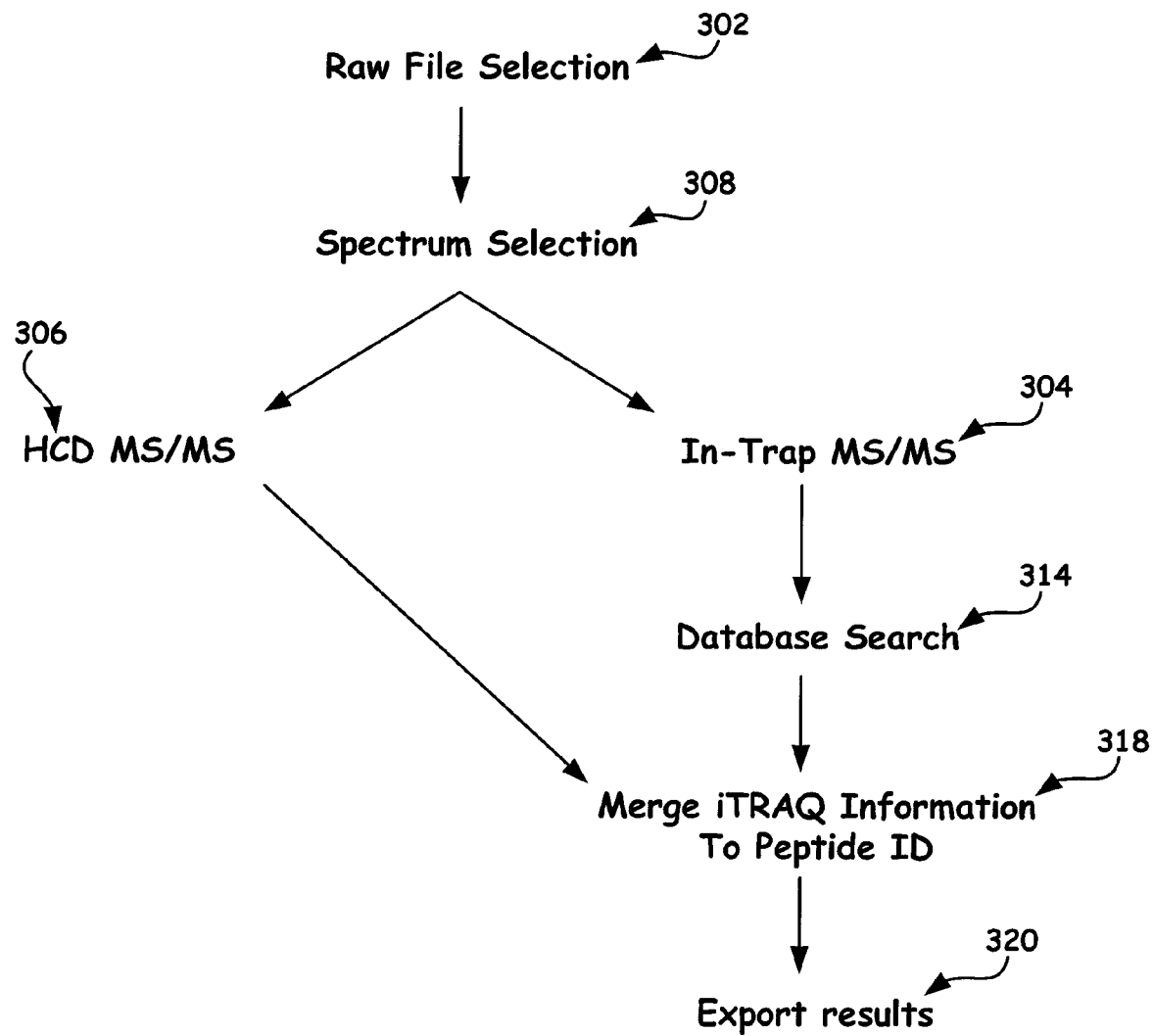
FIG. 3 shows a flow chart representation of a second data merging approach of the present invention.

FIG. 3 depicts an alternative approach for merging MS/MS spectrum obtained using the in-trap and HCD fragmentation techniques. In the FIG. 3 approach and similar to the approach discussed above for FIG. 2, a set of raw files 302 are initially generated representative of the MS/MS spectra of selected peptide precursor ions. For each of the selected ions, MS/MS spectra are acquired using both in-trap fragmentation processes 304, e.g., ETD, CID, PQD, etc., (with the spectra acquired by the ion trap) and an HCD fragmentation process 306 (with the spectra acquired by the Orbitrap). In this method of operation however, a database search 314 is performed using only the in-trap MS/MS spectrum (e.g., the CID, PQD, and/or ETD spectrum) to identify matching peptides or proteins. Data representative of the iTRAQ reporter ions is extracted from the corresponding HCD MS/MS spectrum, merged 318 with the database searched in-trap MS/MS spectrum, wherein quantitation of the identified peptides or proteins is performed using the extracted (iTRAQ) data from the HCD spectrum. The results are thereafter exported 320 so as to enable a user to quantify as well qualify the identified proteins/peptides.

To illustrate the principles of the present invention, the first approach, as shown and as discussed above for FIG. 2, was tested on Multiplexed iTRAQ labeled cell digests samples and analyzed using a nanoLC-ESI-MS/MS with an LTQ Orbitrap XL. Selected parent peptide ions were fragmented alternatively in the HCD collision cell and in the Ion Trap by CID. The collected high mass accuracy and resolution HCD MS/MS spectrum and the low resolution Ion Trap CID MSMS spectrum (triggered from the same full scan MS on the same parent) were then combined together and used for a database search. As part of the procedure, the protein identification and quantification with iTRAQ reporter ions were simultaneously executed. Results of the benefits of the application with merging HCD with CID, whole cell NG1 and based on a MASCOT with the same filters are shown below in Table 1 to thus illustrate the benefits of one embodiment of the present invention.

TABLE 1

|  | #ID peptides | #ID proteins | # quant proteins |
| --- | --- | --- | --- |
| No merging s/n 1 | 802 | 434 | 341 |
| Merged s/n 1 | 950 | 346 | 310 |
| Merged s/n 1.5 | 1294 | 397 | 330 |
| Merged s/n 2 | 1301 | 419 | 326 |

Accordingly, while the total number of quantified proteins slightly decreases from about 341 to about 326, the number of the identified peptides substantially increases from about 802 to about 1301, thus providing better quantitative statistics per protein.

Accordingly, merging MS/MS spectra obtained by HCD and in-trap data have benefits beyond obtaining quantitative and qualitative (structural) information on the same peptide. In certain cases, in-trap spectra, such as CID spectra, are of insufficient quality to provide confident identification. By merging these spectra with corresponding HCD spectra, the quality of the resulting spectrum can increase thereby providing more confident peptide identifications. This effect is especially noticeable for modified (e.g., phosphorylated) peptides which experience predominantly neutral loss (e.g., of a phosphate group) during in-trap processes.

It is generally understood that while the invention has been described in conjunction with the detailed description thereof, the foregoing description is intended to illustrate and not limit the scope of the invention.

The invention claimed is:

1. A mass spectroscopy method for identification and quantification of one or more proteins in a mixture, comprising:
    using a control and data system to generate a raw file;
    identifying by way of said control and data system, a corresponding in-trap induced MS/MS spectra and a high-energy collision-induced dissociation (HCD) spectra resulting from said raw file;
    merging by way of said control and data system, said identified data from said raw file into a spectrum;
    utilizing said control and data system to initiate a database search of said merged spectra ; and
    using said control and data system to export results that match said database search so as to simultaneously quantify and qualify said one or more proteins from said mixture.

2. The method of claim 1, wherein said merging step further comprises adding identified intensity values from said corresponding MS/MS spectra.

3. The method of claim 2, wherein said merging step further comprises: normalizing data resulting in said raw file prior to adding said identified intensity values.

4. The method of claim 2, wherein said merging step further comprises: filtering one or more unwanted data resulting in said raw file prior to adding said identified intensity values.

5. The method of claim 2, wherein said merging step further comprises: correcting for shifts in data resulting in said raw file prior to adding said identified intensity values.

6. The method of claim 1, wherein said merging step provides merged identified data that comprises high-intensity low mass reporter ions and high-intensity sequence ions.

7. The method of claim 6, wherein said high-intensity low mass reporter ions comprises utilizing at least one set of reporter ions selected from iTRAQ and Tandem Mass Tag (TMT) reporter ions.

8. The method of claim 1, wherein said identifying step to provide said corresponding in-trap MS/MS spectra further comprises using at least one fragmentation method selected from: infrared multi-photon photo-dissociation (IRMPD), Pulsed Q Dissociation (PQD), electron transfer dissociation (ETD), and collision-induced dissociation (CID).

9. The method of claim 1, wherein said MS/MS spectra is provided by an ion trap.

10. The method of claim 9, wherein said ion trap comprises a linear ion trap.

11. The method of claim 9, wherein said ion trap comprises an Orbitrap.

12. A mass spectroscopy method for identification and quantification of one or more proteins in a mixture, comprising:
using a control and data system to generate a raw file;
identifying by way of said control and data system, a corresponding in-trap induced MS/MS spectra and a high-energy collision-induced dissociation (HCD) spectra resulting from said raw file;
utilizing said control and data system to identify in-trap induced spectra to initiate a database search;
merging by way of said control and data system, a matched in-trap spectra resulting from said database search with said high energy collision induced (HCD) spectra from said raw file into a spectrum; and
using said control and data system to export results of said merged spectrum so as to simultaneously quantify and qualify said one or more proteins from said mixture.

13. The method of claim 12, wherein said merging step further comprises adding identified intensity values from said matched in-trap spectra and said high energy collision induced (HCD) spectra in said raw file.

14. The method of claim 13, wherein said merging step further comprises: normalizing data resulting from said matched in-trap spectra and said high energy collision induced (HCD) spectra in said raw file prior to adding said identified intensity values.

15. The method of claim 12, wherein said merging step further comprises: filtering one or more unwanted data resulting in said raw file prior to adding said identified intensity values.

16. The method of claim 12, wherein said merging step further comprises: correcting for shifts in data resulting in said raw file prior to adding said identified intensity values.

17. The method of claim 12, wherein said merging step provides merged identified data that comprises high-intensity low mass reporter ions and high-intensity sequence ions.

18. The method of claim 17, wherein said high-intensity low mass reporter ions comprises utilizing at least one set of reporter ions selected from iTRAQ and Tandem Mass Tag (TMT) reporter ions.

19. The method of claim 1, wherein said identifying step to provide said corresponding in-trap MS/MS spectra further comprises using at least one fragmentation method selected from: infrared multi-photon photo-dissociation (IRMPD), Pulsed Q Dissociation (PQD), electron transfer dissociation (ETD), and collision-induced dissociation (CID).

20. The method of claim 1, wherein said MS/MS spectra is provided by an ion trap.

21. The method of claim 3, wherein said ion trap comprises a linear ion trap.

22. The method of claim 3, wherein said ion trap comprises an Orbitrap.

* * * * *